United States Patent [19]
Gertzman

[11] 3,943,933
[45] Mar. 16, 1976

[54] SUTURE WITH RADIATION DEGRADATION NEAR NEEDLE-SUTURE JUNCTION

[75] Inventor: Arthur A. Gertzman, Somerville, N.J.

[73] Assignee: Ethicon, Inc., Somerville, N.J.

[22] Filed: Sept. 25, 1974

[21] Appl. No.: 508,928

[52] U.S. Cl. ........ 128/339; 128/335.5; 204/158 HE
[51] Int. Cl.² .......................................... A61B 17/06
[58] Field of Search ............... 128/334 R, 335.5; 204/158 HE, 159.2; 250/492 R

[56] References Cited
UNITED STATES PATENTS

| | | |
|---|---|---|
| 1,665,216 | 4/1928 | Morton et al. .................... 128/339 |
| 2,014,170 | 9/1935 | Everett .............................. 128/339 |
| 2,910,983 | 11/1959 | Everett .............................. 128/339 |
| 3,349,018 | 10/1967 | Potts ................................ 204/159.2 |
| 3,451,394 | 6/1969 | Bechtol et al. .................... 128/296 |
| 3,758,273 | 9/1973 | Johnson et al. ............. 250/492 R X |
| 3,799,169 | 3/1974 | Beroff et al. ..................... 128/339 |

*Primary Examiner*—Dalton L. Truluck
*Attorney, Agent, or Firm*—Wayne R. Eberhardt

[57] ABSTRACT

A needle-suture combination is provided in which the suture has a radiation-weakened segment adjacent to its attachment to the needle. The radiation-weakened segment permits a surgeon to separate the needle from the suture by a sharp tug.

16 Claims, 3 Drawing Figures

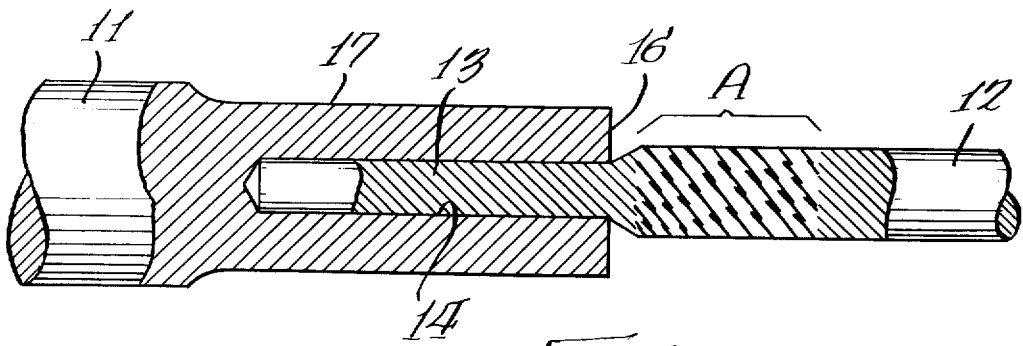
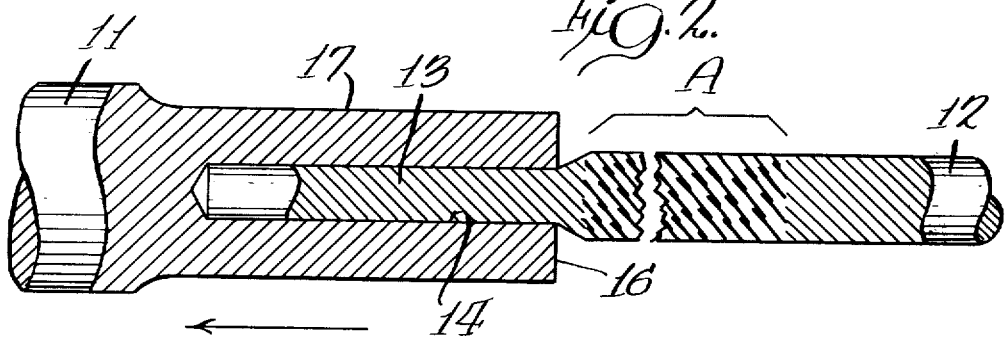
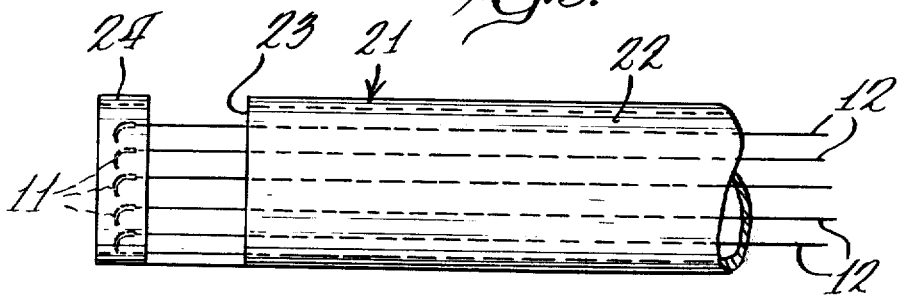

SUTURE WITH RADIATION DEGRADATION NEAR NEEDLE-SUTURE JUNCTION

BACKGROUND OF THE INVENTION

This invention relates to needle-suture combinations and particularly to a combination of a surgical needle with a suture in which the force necessary to separate the needle from the suture is within an acceptable range for convenient removal of the needle from the suture by a sharp tug.

In many surgical procedures, surgeons use a technique which employs a non-needled suture and an eyed needle. The needle is threaded by the nurse and the surgeon takes one or more passes through the tissue using a needleholder. He slips the needle off the suture, returns the needle to the nurse, and is ready for another threaded needle from the nurse. An assistant follows behind and ties the suture.

Some surgeons find that this technique is simpler than using a needled item and cutting the suture with a scissors after each pass. However, the time required for threading results in a significant waste of expensive operating room time.

The security of attachment of eyeless needles to absorbable surgical sutures or to non-absorbable surgical sutures is prescribed in the U.S. Pharmacopoeia, Vol. XVIII at Page 944 (also see U.S. Pharmacopoeia, Vol. XVII, Page 919). It has been the practice of suture manufacturers in the United States and abroad to securely attach the suture to the needle by swaging or with an adhesive so that the minimum pull-out standard recited in the U.S. Pharmacopoeia is met or exceeded.

To avoid the problems discussed above it has been found useful to use needle-suture combinations in which the needle and the suture are readily separable from each other by a sharp tug. Several methods have been devised for preparing needle-suture combinations in which the pull-out values, or the force required for separating the needle from the suture by a straight pull, is within a controlled range.

One approach to this problem is described in copending and co-assigned application Ser. No. 409,974, filed Oct. 26, 1973. This approach involves inserting into a drilled hole in the blunt end of the needle one end of the suture which has been sized with a resin and is smaller in diameter than the remainder of the suture and then swaging the needle at its blunt end to provide a controlled degree of compression to the end of the suture within the hole. This approach is restricted to needle-suture combinations wherein the suture is of large size, i.e., size 4/0 and larger (diameter greater than 7.0 mils), and produces average pull-out values of 3 to 26 ounces, indicating that it takes a straight pull of the magnitude within that range to separate the needle from the suture.

Another approach to the problem is described in copending and co-assigned application Ser. No. 446,174, filed by Robert Barclay Duncan on Feg. 27, 1974. In this approach sufficient tension is applied to the suture in a swaged needle-suture combination to move the suture relative to the needle recess and the tension is released when the force drops to the range desired for the pull-out value, the range varying for different sizes of suture. This approach is applicable to a broader range of suture sizes than the approach of application Ser. No. 409,974, and is applicable to sizes as small as 8/0.

The present invention provides another approach to the problem and provides for easy separation of needles from needle-suture combinations without requiring any change in the manner of manufacture of the needle-suture combinations. It also permits the conversion of existing stocks of needle-suture combinations to products from which the needles can be separated by application of moderate force.

BRIEF SUMMARY OF THE INVENTION

In accordance with the present invention there is provided a needle-suture combination comprising a needle having a sharp end and a blunt end and having a recess at said blunt end, a suture having one tip positioned within said recess, means retaining said tip of said suture within said recess to attach said suture to said needle, and a radiation-weakened segment in said suture adjacent the location of its attachment to said needle It is essential that the suture be made of a material which is subject to weakening after exposure to radiation, as will be explained.

Radiation-weakening is preferably achieved after the needle-suture combination has been assembled by the insertion of the suture tip into the recess in the blunt end of the needle and by its attachment therein by swaging of the blunt end of the needle or by an adhesive. In some cases, it may be more convenient to subject a segment of a suture to radiation weakening before attachment of the suture to a needle.

Radiation-weakening is achieved by exposure of a segment of the suture at or near its point of attachment to the needle to a sufficient dose of beta or gamma radiation to reduce the tensile strength in the irradiated segment to a desired value. The necessary dose, or exposure, to achieve the desired weakening is dependent on the nature of the suture material and its diameter and upon the degree of weakening desired. In the case of sutures of small diameter which have pull-out values within the desired range, radiation-weakening is, of course, unnecessary.

For suture materials readily susceptible to radiation-weakening in sutures of small diameters and requiring only slight weakening to be within the desired range of pull-out values, useful radiation-weakening may be achieved with radiation doses as low as about 5 megarads. For suture materials which are more difficult to weaken by irradiation in sutures of larger diameter it may be necessary to provide a dose of 200 megarads, or more, before the rupture strength of the suture is reduced to a practical value for easy separation of the needle from the suture.

The radiation used for localized suture weakening in accordance with this invention may comprise either a high energy electron beam, of the type produced by a linear electron accelerator, or a high energy beam of electromagnetic radiation of extremely short wave length, of the type generated by cobalt-60 or by a high energy X-ray generator. These forms of radiation are conventionally referred to as "beta" and "gamma" radiation, respectively. An electron accelerator capable of delivering a large dose of energy in a short time is preferred.

Radiation generators suitable for use in this invention include those frequently used by manufacturers of needle-suture combinations for sterilization purposes. For localized suture weakening, however, the arrangement is altered so that the suture passes transversely across the path of the beam instead of longitudinally, thereby isolating the radiation effect to a small segment of the suture length; and the arrangement is also altered to permit a plurality of passes of the suture segment to be weakened under the radiation beam and to thereby subject the segment to the cumulative dosage of such a plurality of passes. The sutures are preferably aligned parallel to each other in a grooved holder encased within a lead casing or other suitable shielding, except for an exposed open slot which permits the radiation to pass through the casing and act upon a short segment of each suture at or near its junction to its needle.

Fiber-forming materials suitable for sutures which have been found to be susceptible to radiation-weakening and useful in the practice of this invention include cellulose and cellulose esters including cotton, linen, viscose rayon and cellulose acetate; polyolefins including polypropylene and polyethylene; vinyl polymers, including polyvinyl alcohol, polyvinyl acetate and polyvinylidene chloride; acrylic polymers, such as polyacrylonitrile; and homopolymers and copolymers of lactide and glycolide. It has also been found that certain other suture materials are highly resistant to radiation-weakening; and sutures made of these materials are unsuitable for weakening by the method of this invention. Such radiation-resistant suture materials include nylon, silk and polyethylene terephthalate.

BRIEF DESCRIPTION OF THE DRAWINGS

The invention will become more readily apparent upon consideration of the following detailed description when taken in connection with the accompanying drawings wherein:

FIG. 1 is an enlarged fragmentary elevation, partly in cross section of the needle-suture combination of this invention at the juncture of the needle and the suture;

FIG. 2 is a view similar to that of FIG. 1 but showing rupture of the suture adjacent its juncture to the needle after application of sufficient tension thereto; and FIG. 3 is an enlarged fragmentary elevation of a holder for the exposure of a plurality of needle-suture combinations to radiation at the desired sites with a portion broken away to show the holder interior.

DETAILED DESCRIPTION

As may be seen in FIGS. 1 and 2, needle 11 and suture 12 are attached to each other by the insertion of end 13 of the suture into hole 14 in blunt end 16 of the needle. The blunt end of the needle is subjected to cold pressure to produce swaged portion 17 of the needle, resulting in the distortion of hole 14 and the compression of suture tip 13 within the hole to affix the suture end within the hole.

A short segment A of the suture is then subjected to beta- or gamma-radiation to alter and weaken its structure, as represented schematically in FIGS. 1 and 2 by zig-zag cross-hatching. When the needle is tugged after the suture has been pulled through the desired tissues in the surgical procedure, the suture ruptures in radiation-weakened segment A, as shown in FIG. 2.

FIG. 3 shows a holder suitable for exposing a plurality of needle-suture combinations to radiation at the desired sites. Holder 21 comprises a circular pipe 22 which is either made of lead, or which includes a shielding of lead or other suitable material. Slot 23 is provided near one end 24 of the pipe to permit the passage of radiation therethrough. Within pipe 22 there are a plurality of needle-suture assemblies, aligned parallel to each other (by means not shown) with needles 11 at end 24 and with a segment of each suture 12 exposed to radiation through slot 23. Cooling means (not shown) are provided to prevent excessive temperatures in the shielding.

The treatment of needle-suture combinations to provide the desired radiation weakening involves the insertion of a plurality of appropriately aligned needle-suture combinations into pipe 22. Pipe 22 is thereafter moved into position under a concentrated beam of radiation so that the radiation passes through slot 23 at one end thereof and acts upon the suture portions immediately under the slot. Pipe 22 is then rotated about its axis, keeping the concentrated radiation beam passing through the slot so that each suture will receive a radiation dose in the desired location adjacent its juncture to its needle. The procedure may be repeated until the cumulative radiation dose is sufficient to provide the desired degree of weakening.

EXAMPLE 1

Needle-suture combinations, each made of a needle holding a size 0 polypropylene monofilament suture were subjected to varying cumulative doses of gamma radiation at the site on each suture of its junction to its needle. The gamma radiation was produced by cobalt-60 in apparatus usually used to sterilize the needle-suture combinations, except that most of the length of each suture was protected from radiation by encasement in lead. At each test level of cumulative radiation dosage, 10 needle-suture combinations were tested to determine the force necessary to produce a suture break and both the range and average values were determined.

EXAMPLE 2

The procedure of Example 1 was repeated, except that the needle-suture combinations comprised needles holding sizes 2–0 white twisted cotton sutures.

The average force required for suture break and the range at different levels of exposure in Examples 1 and 2 were as follows:

| Radiation Dose | Example 1 Average (lbs) | Range (lbs) | Example 2 Average (lbs) | Range (lbs) |
|---|---|---|---|---|
| None | 8.7 | 7.8–9.6 | 5.4 | 5.2–5.6 |
| 2.5 megarads | 7.1 | 6.4–8.3 | 4.6 | 3.4–5.0 |
| 7.5 megarads | 5.8 | 4.2–6.9 | 4.0 | 3.2–4.7 |
| 12.5 megarads | 5.1 | 4.2–6.1 | 3.5 | 2.3–4.0 |
| 17.5 megarads | 4.5 | 3.8–5.4 | 2.8 | 1.9–3.0 |
| 22.5 megarads | 4.3 | 3.5–5.4 | 2.5 | 2.0–3.0 |
| 27.5 megarads | 3.3 | 2.5–4.2 | | |
| 32.5 megarads | 3.5 | 1.7–4.6 | | |

EXAMPLES 3 TO 11

A plurality of sutures in two sizes each of three different suture materials were subjected to repeated doses of gamma radiation from a cobalt-60 source in 5 megarad increments at localized areas thereof while the remainder of the length of each suture was shielded from the radiation. At each test level of cumulative radiation dosage, 10 sutures were subjected to tension to determine the force necessary to produce a suture break. The average values (in pounds) were as follows:

| Example | 3 | 4 | 5 | 6 | 7 | 8 | 9 | 10 | 11 |
|---|---|---|---|---|---|---|---|---|---|
| Suture Type | polypropylene monofilament | | | twisted cotton | | | poly(lactide-co-glycolide) braid | | |
| Suture Size | 4–0 | 3–0 | 2–0 | 4–0 | 3–0 | 2–0 | 3–0 | 1 | 5–0 |
| Megarads | | | | | | | | | |
| 0 | 3.4 | 4.5 | 7.6 | 2.63 | 4.3 | 5.7 | 7.7 | 24.2 | 3.51 |
| 5 | 1.93 | | 4.7 | 2.23 | | 6.8 | 7.8 | 22.9 | |
| 10 | 1.60 | | 3.62 | 1.90 | | 3.93 | 7.24 | 21.1 | |
| 15 | 1.33 | | 3.30 | 1.68 | | 3.4 | 6.6 | 19.6 | |
| 20 | 1.30 | | 2.80 | 1.45 | | 2.93 | 6.2 | 18.2 | |
| 25 | 1.20 | | 2.43 | 1.4 | | 2.54 | 5.9 | 17.1 | |
| 30 | 0.78 | | 2.26 | 1.01 | | 2.46 | 5.4 | 15.9 | |
| 35 | 0.78 | 1.70 | 2.26 | 0.95 | 1.76 | 2.23 | 5.32 | 14.9 | 1.91 |
| 40 | 0.64 | | 2.10 | 0.79 | | 2.00 | 4.70 | 14.9 | |
| 45 | 0.69 | 1.59 | 1.97 | 0.70 | 1.52 | 1.72 | 4.60 | 13.4 | 1.65 |
| 55 | | 0.91 | | | 0.86 | | | | 0.95 |

As may be seen from the foregoing data the degree of radiation-weakening at equivalent radiation dosage varies with both the nature of the suture material and its cross-sectional area although the percentage of radiation-weakening for a particular material at a particular dosage is approximately the same, regardless of its cross-sectional area. In general, and as an approximation, polypropylene and cotton sutures require from about 0.4 to about 0.7 megarads of gamma radiation for each 1% of loss of strength at the radiation-weakened segment. Poly(lactide-co-glycolide) sutures require about 0.6 to about 1.2 megarads of gamma radiation for each 1% of loss of strength at the radiation-weakened segment. Suitable radiation dosages for other suture materials may be determined by those skilled in the art with a small amount of experimentation by the methods described above.

The invention has been described with respect to preferred embodiments but other embodiments and modifications will be apparent to those skilled in the art.

What is claimed is:

1. A needle-suture combination comprising a needle having a sharp end and a blunt end and having a recess at said blunt end, and a suture made of a material selected from the group consisting of cellulose and cellulose esters, polyolefins, vinyl polymers, acrylic polymers and homopolymers and copolymers of lactide and glycolide, said suture having one tip positioned within said recess, means retaining said tip of said suture within said recess to attach said suture to said needle, and a radiation-weakened segment in said suture adjacent the location of its attachment to said needle and exterior of said recess, said weakened segment having a breaking strength of from about 3 to 26 ounces, whereby said needle can readily be separated from said suture by applying a pulling force to said needle to break said weakened segment.

2. The needle-suture combination of claim 1, wherein said suture comprises a monofilament.

3. The needle-suture combination of claim 1, wherein said suture comprises a multifilament suture.

4. The needle-suture combination of claim 1, wherein said suture comprises polypropylene.

5. The needle-suture combination of claim 1, wherein said suture comprises cotton.

6. The needle-suture combination of claim 1, wherein said suture comprises linen.

7. The needle-suture combination of claim 1, wherein said suture comprises polylactide.

8. The needle-suture combination of claim 1, wherein said suture comprises polyglycolide.

9. The needle-suture combination of claim 1, wherein said suture comprises poly(lactide-co-glycolide).

10. A method of altering a needle-suture combination in which a needle is attached to a suture made of a material selected from the group consisting of cellulose and cellulose esters, polyolefins, vinyl polymers, acrylic polymers, and homopolymers and copolymers of lactide and glycolide which comprises exposing a segment of said suture located adjacent to and exterior of the needle to sufficient radiation of the class consisting of beta radiation and gamma radiation to reduce the breaking strength of said segment to about 3 to 26 ounces while shielding the remainder of said suture from said radiation.

11. The method of claim 10 wherein said radiation is gamma radiation at a cumulative dosage from about 5 to about 200 megarads.

12. The method of claim 10 wherein said radiation is generated from a cobalt-60 source.

13. The method of claim 10, wherein said radiation is generated as a high energy electron beam.

14. The method of claim 10 wherein said suture is made of cotton and said radiation dosage is from about 0.4 to about 0.7 megarads per percent decrease in rupture strength at the radiation site based on the original rupture strength of the suture.

15. The method of claim 10 wherein said suture is made of polypropylene and said radiation dosage is from about 0.4 to about 0.7 megarads per percent decrease in rupture strength at the radiation site based on the original rupture strength of the suture.

16. The method of claim 10 wherein said suture is made of poly(lactide-co-glycolide) and said radiation dosage is from about 0.6 to about 1.2 megarads per percent decrease in rupture strength at the radiation site based on the original rupture strength of the suture.

* * * * *